United States Patent
Lee et al.

(10) Patent No.: US 10,191,018 B2
(45) Date of Patent: Jan. 29, 2019

(54) DUAL ONLINE LIQUID CHROMATOGRAPHY DEVICE AND CONTROL METHOD THEREOF

(71) Applicant: KOREA UNIVERSITY RESEARCH AND BUSINESS FOUNDATION, Seoul (KR)

(72) Inventors: Sang-Won Lee, Seoul (KR); Hangyeore Lee, Seoul (KR)

(73) Assignee: KOREA UNIVERSITY RESEARCH AND BUSINESS FOUNDATION, Seoul (KR)

(*) Notice: Subject to any disclaimer, the term of this patent is extended or adjusted under 35 U.S.C. 154(b) by 216 days.

(21) Appl. No.: 15/129,543

(22) PCT Filed: Oct. 22, 2014

(86) PCT No.: PCT/KR2014/009963
§ 371 (c)(1),
(2) Date: Sep. 27, 2016

(87) PCT Pub. No.: WO2015/147397
PCT Pub. Date: Oct. 1, 2015

(65) Prior Publication Data
US 2017/0176400 A1 Jun. 22, 2017

(30) Foreign Application Priority Data
Mar. 28, 2014 (KR) .................. 10-2014-0036548

(51) Int. Cl.
*B01D 15/18* (2006.01)
*G01N 30/00* (2006.01)
(Continued)

(52) U.S. Cl.
CPC .......... *G01N 30/468* (2013.01); *G01N 30/20* (2013.01); *B01D 15/1864* (2013.01);
(Continued)

(58) Field of Classification Search
CPC .......... G01N 30/468; G01N 2030/201; G01N 2030/202; G01N 2030/207
See application file for complete search history.

(56) References Cited

U.S. PATENT DOCUMENTS

2003/0168392 A1 9/2003 Masuda et al.

FOREIGN PATENT DOCUMENTS

| CN | 1785476 | 6/2006 |
|----|---------|--------|
| CN | 103063753 | 4/2013 |

(Continued)

OTHER PUBLICATIONS

Link, et al., "Direct analysis of protein complexes using mass spectrometry", Nature Biotechnology, vol. 17, Jul. 1999.
(Continued)

*Primary Examiner* — Paul M. West
(74) *Attorney, Agent, or Firm* — Duane Morris LLP; J. Rodman Steele, Jr.; Gregory M. Lefkowitz (57) ABSTRACT

A dual online liquid chromatography device according to an embodiment of the present invention comprises: a first pump for injecting a first solvent or a mixed solution containing the first solvent and a second solvent; a second pump for injecting the first solvent or the mixed solution containing the first and second solvents; a specimen intake valve connected to the first pump and a specimen injector for injecting a specimen; a column selection valve connected to the second pump and the specimen intake valve; and a dual column valve including a plurality of ports, one side of which is connected to the column selection valve and an opposite side of which is connected to a first column and a second column.

15 Claims, 3 Drawing Sheets

(51) Int. Cl.
*G01N 30/08* (2006.01)
*G01N 30/20* (2006.01)
*G01N 30/46* (2006.01)

(52) U.S. Cl.
CPC ....... *G01N 30/08* (2013.01); *G01N 2030/009* (2013.01); *G01N 2030/201* (2013.01); *G01N 2030/202* (2013.01); *G01N 2030/207* (2013.01)

(56) References Cited

FOREIGN PATENT DOCUMENTS

| EP | 1536228 | 6/2005 |
| EP | 2891881 | 8/2015 |
| JP | 2010-271300 | 2/2010 |
| KR | 1007575120000 | 9/2007 |
| KR | 201020000538 | 1/2012 |
| WO | 2011/162575 | 12/2011 |
| WO | 2014/032285 | 3/2014 |

OTHER PUBLICATIONS

Chen, et al., Large Scale Protein Profiling by Combination of Protein Fractionation and Multidimensional Protein Identification Technology (MudPIT)*, The American Society for Biochemistry and Molecular Biology, Inc., 2006.

Kim, et al., "Develpment of Ultra-High Pressure Capillary Reverse-Phase Liquid Chromatograpy/Tandem Mass Spectrometry for High-Sensitive and High-Throughput Proteomics", Bull. Koean Chem. Soc., vol. 25, No. 12, 2004.

DUAL ONLINE LIQUID CHROMATOGRAPHY DEVICE AND CONTROL METHOD THEREOF

CROSS-REFERENCE TO RELATED APPLICATIONS

This application is a § 371 national stage entry of International Application No. PCT/KR 2014/009963, filed Oct. 22, 2014, which claims priority to Korean Patent Application No. 10-2014-0036548 filed Mar. 28, 2014, the entire contents of which are incorporated herein by reference.

TECHNICAL FIELD

The present invention relates to a dual online liquid chromatography device and a control method thereof.

BACKGROUND ART

The fields of -omics, which started to be studied after the completion of the Human Genome Project, systemically deal with qualitative/quantitative information such as nucleic acids, proteins, carbohydrates and fats and are the most actively researched analysis chemical fields. Representative omics are proteomics involving protein analysis and metabolomics involving metabolites. In these fields, a variety of methods may be used to analyze peptides or low-molecular weight substances. Spectroscopic analysis such as nuclear magnetic resonance, infrared spectroscopy and Raman spectroscopy, as well as mass spectrometry in which masses of substances are measured after ionization by various methods may be used.

Of them, regarding mass spectrometry, analytical technology such as electrophoresis, chromatography, or ultracentrifugation should be used to measure the mass of biopolymers such as proteins till the late 1970's. However, these methods have considerably low accuracy of analysis results because many analysis errors are generated by factors such as shape, hydrophilic groups and hydrophobic groups and dissociation levels of biopolymers when fluids flow.

Accordingly, two new ionization technologies (ESI and MALDI) to overcome these difficulties were introduced in the early of 1990s, thus realizing mass and structure analysis of proteins and mass spectrometry starts to play a great role in the proteomics, the study field thereof.

In particular, on-line solid phase extraction/capillary reverse-phase liquid chromatography is considered very important in proteome research due to excellent analysis efficiency. On-line solid phase extraction/capillary reverse-phase liquid chromatography enables effective analysis of fine amounts of biomaterials and identification of fine amounts of proteins at high efficiency due to wide analyte-solid reaction range.

As a method of analyzing proteins, mass spectrometry-based methods function as a standard analysis platform for proteome research. Representative examples of mass spectrometry-based methods include shotgun, bottom-up methods and the like which involve degradation of proteins into peptides by hydrolysis before analysis using a mass spectrometer. This hydrolysis causes formation of peptide fragments which can be easily ionized and detected in a mass spectrometer while increasing solubility of bio-samples. However, this process inevitably causes complexity of samples. For example, in the simplest proteome, the yeast proteome, 300,000 or more peptide fragments are produced from about 6,000 various proteins.

Accordingly, in an attempt to solve this sample complexity, a variety of methods such as on-/off-line multidimensional protein identification technology described in Non-patent document 1 were developed, but the need for improvement in efficiency and sensitivity of liquid chromatography columns still remains.

In this case, it was known that the sensitivity of liquid chromatography/mass spectrometry tests can be rapidly increased when the inner diameter of separation columns is decreased while maintaining a predetermined length of separation columns, as described in Non-patent document 2.

However, conventional on-line reverse-phase liquid chromatography devices have a problem of taking a long time for column equilibration or re-use, when capillary columns having a large length and a small inner diameter are filled with a hydrophobic medium. For example, to re-use a column with a length of 1 m and an inner diameter of 75 µm, at least two hours are required for equilibration.

Accordingly, conventional on-line reverse-phase liquid chromatography devices have problems of considerable loss in terms of cost and time, due to dead time at which other analysis processes cannot be conducted during cleaning and equilibration or regeneration of columns.

RELATED ART DOCUMENT

Non-Patent Document (Non-patent document 1) Non-patent document 1: Link, A. J., Eng, J., Schieltz, D. M., Carmack, E., et al., Nat. Biotechnol. 1999, 17, 676-682; Chen, E. I., Hewel, J., Felding-Habermann, B., Yates, J. R. III, Mol. Cell. Proteomics 2006, 5, 53-56.

(Non-patent document 2) Non-patent document 2: Kim, M.-S., Choie, W.-S., Shin, Y. S., Yu, M. H., Lee, S.-W., Bull. Korean Chem. Soc. 2004, 25, 1833-1839.

DISCLOSURE

Technical Problem

Therefore, it is one object of the present invention to provide a dual online liquid chromatography device which conducts analysis test on a column at one side while conducting cleaning and equilibration on a column at the other side.

It is another object of the present invention to provide a method of controlling a dual online liquid chromatography device which conducts analysis test on a column at one side while conducting cleaning and equilibration on a column at the other side.

Technical Solution

In accordance with one aspect of the present invention, the above and other objects can be accomplished by the provision of a dual online liquid chromatography device including a first pump for injecting a first solvent or a mixed solution containing the first solvent and a second solvent, a second pump for injecting the first solvent or the mixed solution containing the first solvent and the second solvent, a sample intake valve connected to the first pump and a sample injector for injecting a sample, a column selection valve connected to the second pump and the sample intake valve, and a dual column valve having one side connected to the column selection valve and the other side connected to the first column and the second column, and including a plurality of ports.

The sample intake valve may include a sample inlet port to which the sample is fed from the sample injector, a first sample loop connection port and a second sample loop connection port provided at opposite ends of the sample loop, a sample outlet port for discharging the remaining sample, a solvent inlet port connected to the first pump and to which the first solvent or the mixed solution containing the first solvent and the second solvent is fed, and a solvent outlet port connected to the column selection valve. The column selection valve may include a first inlet port connected to the sample intake valve, a first outlet port connected to one side of the dual column valve, a second inlet port connected to the second pump, and a second outlet port connected to the other side of the dual column valve.

The dual column valve may include a first column port connected to the first column, a solid phase extraction column selection port and a solid phase extraction column channel port constituting opposite ends of the first solid phase extraction column (SPE1), a solid phase extraction column inlet port connected to one side of the column selection valve and selectively connected to the solid phase extraction column selection port or the solid phase extraction column channel port, a first outlet port adjacent to the solid phase extraction column channel port, a second outlet port adjacent to the first outlet port, a second solid phase extraction column selection port and a second solid phase extraction column channel port constituting opposite ends of the second solid phase extraction column (SPE2), a second solid phase extraction column inlet port connected to the other side of the column selection valve and selectively connected to the second solid phase extraction column selection port and the second solid phase extraction column channel port, and a second column port connected to the second column.

The dual column valve may form a first fluid communication with the first column or the first solid phase extraction column (SPE1), and a second fluid communication with the second column or the second solid phase extraction column (SPE1), and the dual column valve may selectively have a mode of simultaneously conducting separate analysis of the sample using the first fluid communication, and cleaning and equilibration of the second fluid communication, and a mode of simultaneously conducting separate analysis of the sample using the second fluid communication, and cleaning and equilibration of the first fluid communication.

In another aspect of the present invention, provided is a method of controlling a dual online liquid chromatography device including (A) conducting an initial mode including equilibration of a first column or a first solid phase extraction column (SPE1), equilibration of a second column and a second solid phase extraction column (SPE2) and storing a sample in a sample loop, (B) conducting a first mode including injecting the sample of the sample loop into the first solid phase extraction column (SPE1) together with a first solvent, (C) conducting a second mode including injecting and storing another sample into the sample loop, separate elution of the sample injected into the first solid phase extraction column (SPE1), and equilibration of the second column and the second solid phase extraction column (SPE2) and (D) conducting a third mode including equilibration of the first solid phase extraction column (SPE1), and injecting the another sample of the sample loop together with the first solvent into the second solid phase extraction column (SPE2), and (E) conducting a fourth mode including equilibration of the first column and the first solid phase extraction column (SPE1) and separate elution of another sample injected into the second solid phase extraction column (SPE2).

The step (E) may further include storing another sample in the sample loop.

The steps (A) to (E) may be repeatedly conducted depending on the frequency of separate analysis of the sample or the number of the samples.

The step (A) may include injecting the first solvent from the first pump using fluid communication with the first column and the first solid phase extraction column (SPE1) to conduct equilibration of the first column and the first solid phase extraction column (SPE1) by, and injecting the first solvent from the second pump using fluid communication with the second column and the second solid phase extraction column (SPE2) to conduct equilibration of the second column and the second solid phase extraction column (SPE2).

The step (A) may further include (A-1) injecting the mixed solution containing the first solvent and the second solvent from the first pump using fluid communication with the first column and the first solid phase extraction column (SPE1) to conduct cleaning of the first column and the first solid phase extraction column (SPE1), and injecting the mixed solution containing the first solvent and the second solvent from the second pump using fluid communication with the second column and the second solid phase extraction column (SPE2) to conduct cleaning of the second column and the second solid phase extraction column (SPE2), and (A-2) injecting the first solvent from the first pump using fluid communication with the first column and the first solid phase extraction column (SPE1) to conduct equilibration of the first column and the first solid phase extraction column (SPE1), and injecting the first solvent from the second pump using fluid communication with the second column and the second solid phase extraction column (SPE2) to conduct equilibration of the second column and the second solid phase extraction column (SPE2).

The step (B) may further include further injecting the first solvent into the first solid phase extraction column (SPE1) so that salts are dissolved in the first solvent and discharged through the first outlet port to concentrate and desalt the sample in the first solid phase extraction column (SPE1).

In the step (C), separate elution of the sample injected into the first solid phase extraction column (SPE1) may be carried out while flowing, by the second pump, the mixed solution containing the first solvent and the second solvent via the first solid phase extraction column (SPE1) to the first column, wherein a ratio of the first solvent and the second solvent is changed over time.

In the step (C), cleaning and equilibration of the second column and the second solid phase extraction column (SPE2) may include cleaning including flowing, by the first pump, the mixed solution containing the first solvent and the second solvent via the second solid phase extraction column (SPE2) to the second column, while increasing a content of the second solvent, and equilibration including continuously flowing the first solvent, by the first pump, via the second solid phase extraction column (SPE2) to the second column.

In the step (D), the injecting another sample in the sample loop together with the first solvent into the second solid phase extraction column (SPE2) may further include further injecting the first solvent into the second solid phase extraction column (SPE2) so that salts are dissolved in the first solvent and discharged through the second outlet port to concentrate and desalt the sample in the second solid phase extraction column (SPE2).

In the step (E), the separate elution of another sample injected into the second solid phase extraction column (SPE2) may be carried out while flowing the mixed solution containing the first solvent and the second solvent by the second pump via the second solid phase extraction column (SPE2) to the second column, wherein a ratio of the first solvent and the second solvent is changed over time.

In the step (E), the cleaning and equilibration of the first column and the first solid phase extraction column (SPE1) may include cleaning including flowing, by the first pump, the mixed solution containing the first solvent and the second solvent via the first solid phase extraction column (SPE1) to the first column, while increasing a content of the second solvent, and equilibration including continuously flowing the first solvent, by the first pump, via the first solid phase extraction column (SPE1) to the first column.

The features and advantages of the present invention will be more clearly understood based on the following detailed description provided with reference to the annexed drawings.

First, the terms and words used in the present specification and claims should not be construed to be limited to common or dictionary meanings and should be construed as a meaning and concept fit to the technological concept and scope of the present invention based on the principle that an inventor can define the concept of the terms appropriately to describe his/her invention in the best manner.

Effects of the Invention

The dual online liquid chromatography device according to the present invention has an effect of continuously conducting analysis regardless of dead time at which analysis data cannot be obtained during equilibration of conventional columns.

The method of controlling the dual online liquid chromatography device has an effect of simultaneously and repeatedly conducting separate analysis of samples using three valves and equilibration using an injected solvent.

DESCRIPTION OF DRAWINGS

The above and other objects, features and other advantages of the present invention will be more clearly understood from the following detailed description taken in conjunction with the accompanying drawings, in which.

BEST MODE

The objects, certain advantages and novel features of the present invention will be more clearly understood from the following detailed description and preferred embodiments associated with the annexed drawings. When the reference numbers refer to elements of respective drawings in the specification, it should be noted that identical reference numerals refer to identical elements although the elements are shown in different drawings. In addition, terms such as "first" and "second" may be used to describe a variety of elements, but the elements are not limited to the terms. The terms are used only to distinguish one element from another element. In addition, a detailed description of parts unrelated to the description will be omitted for clarity when the detailed description makes the subject matter obscure.

Figure 1:
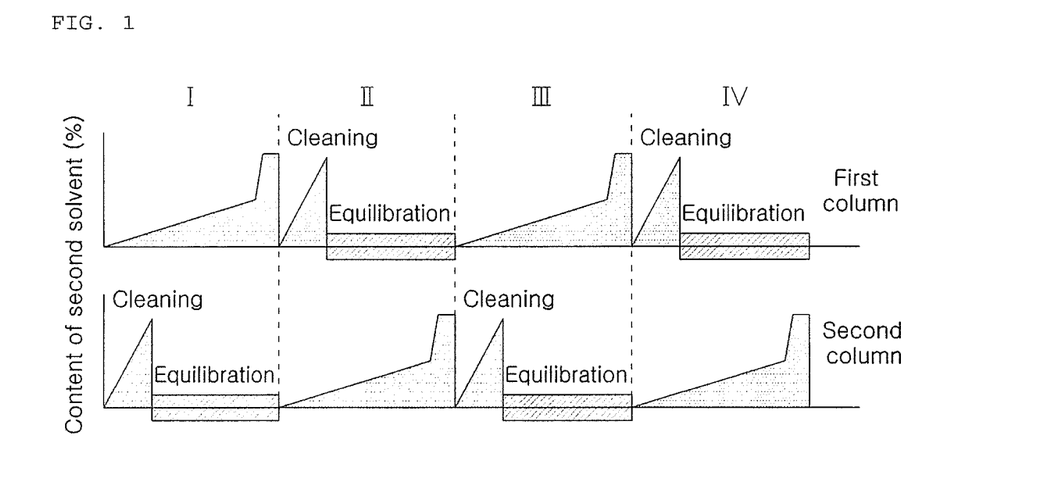
FIG. 1 is a graph illustrating an operation of a dual online liquid chromatography device according to an embodiment of the present invention.
Figure 2A:
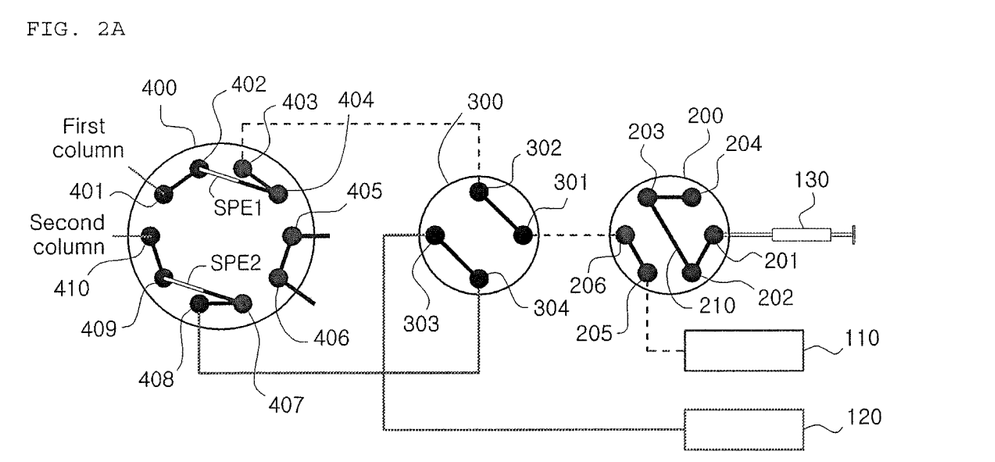
FIG. 2A shows an example of an operation of an initial mode of a dual online liquid chromatography device according to an embodiment of the present invention.
Figure 2B:
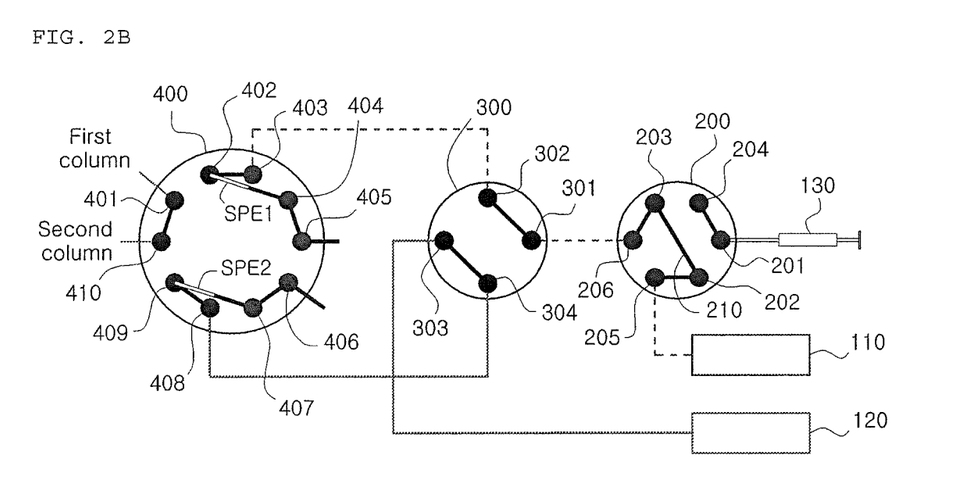
FIG. 2B shows an example of an operation of a first mode of a dual online liquid chromatography device according to an embodiment of the present invention.
Figure 2C:
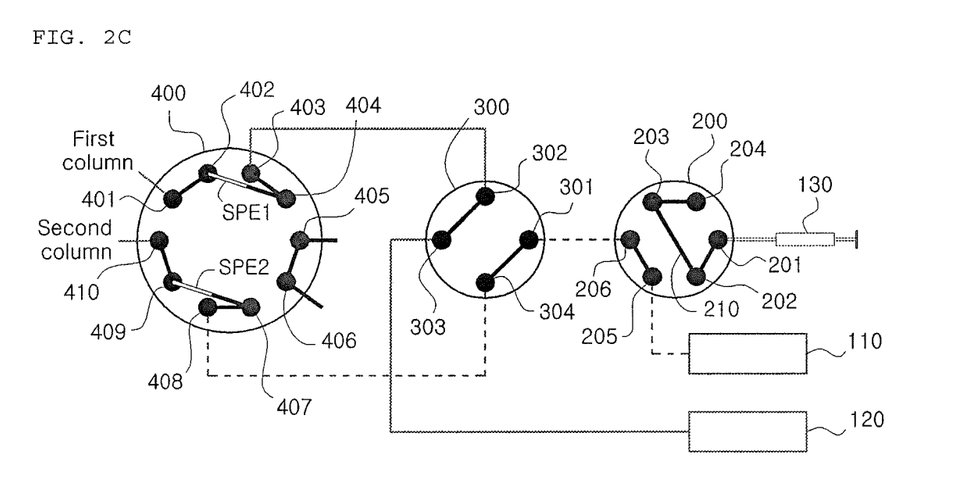
FIG. 2C shows an example of an operation of a second mode of a dual online liquid chromatography device according to an embodiment of the present invention.
Figure 2D:
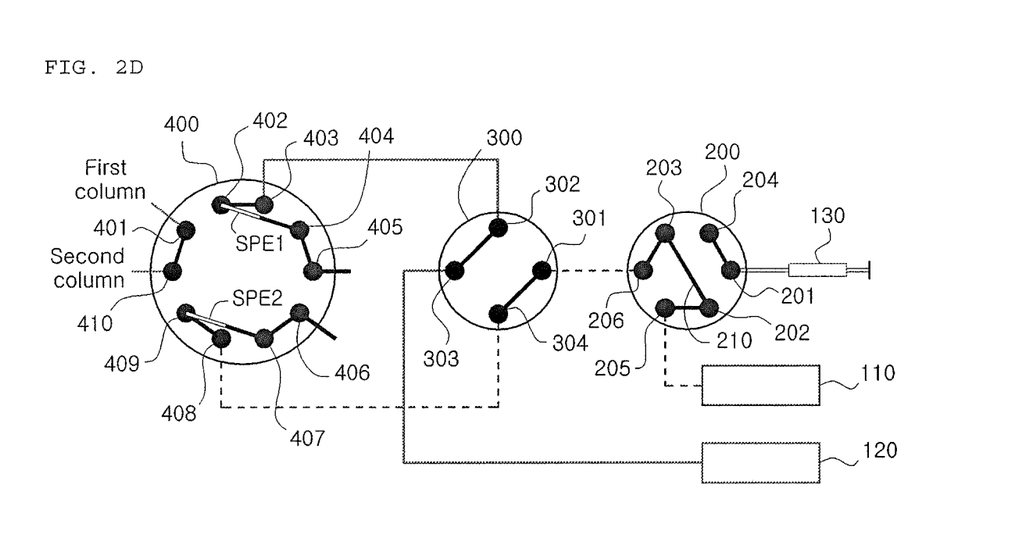
FIG. 2D shows an example of an operation of a third mode of a dual online liquid chromatography device according to an embodiment of the present invention.
Figure 2E:
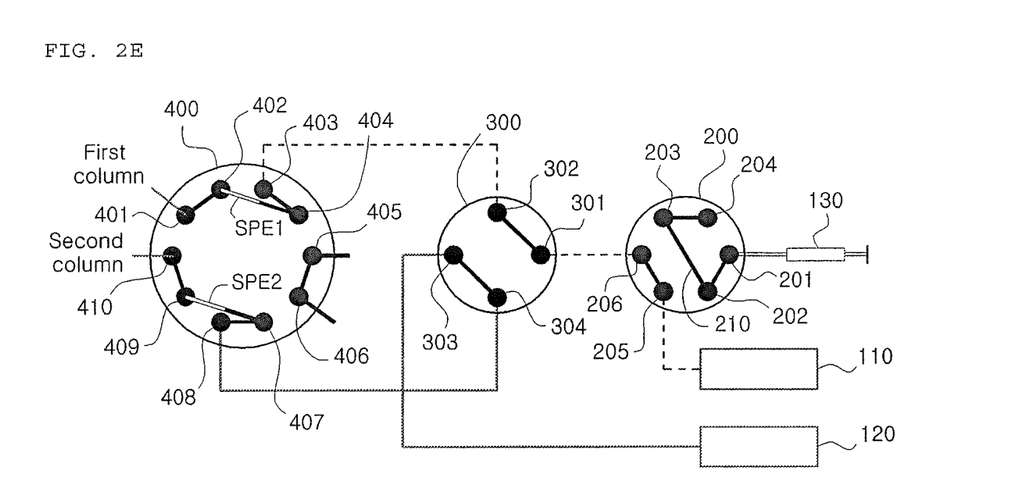
FIG. 2E shows an example of an operation of a fourth mode of a dual online liquid chromatography device according to an embodiment of the present invention.

Hereinafter, preferred embodiments of the present invention will be described in detail with reference to the annexed drawings. FIG. 1 is a graph illustrating an operation of a dual online liquid chromatography device according to an embodiment of the present invention, FIG. 2A shows an example of an operation of an initial mode of a dual online liquid chromatography device according to an embodiment of the present invention, FIG. 2B shows an example of an operation of a first mode of a dual online liquid chromatography device according to an embodiment of the present invention, FIG. 2C shows an example of an operation of a second mode of a dual online liquid chromatography device according to an embodiment of the present invention, FIG. 2D shows an example of an operation of a third mode of a dual online liquid chromatography device according to an embodiment of the present invention, and FIG. 2E shows an example of an operation of a fourth mode of a dual online liquid chromatography device according to an embodiment of the present invention.

First, the dual online liquid chromatography device according to an embodiment of the present invention, as shown in FIGS. 2A to 2E, includes a first pump 110, a second pump 120, a sample intake (feed) valve 200 connected to the first pump 110 and a sample injector 130, a column selection valve 300 connected to the second pump 120 and the sample intake valve 200, and a dual column valve 400 which is connected to the column selection valve 300 and includes a plurality of ports including a first reverse-phase liquid chromatography column (hereinafter, referred to as a "first column"), a second reverse-phase liquid chromatography column (hereinafter, referred to as a "second column"), a first solid phase extraction column (SPE1) and a second solid phase extraction column (SPE2).

The first pump 110 and the second pump 120 are pumps for injecting a first solvent or a mixed solution containing the first solvent and a second solvent, the first solvent is a hydrophilic solvent, for example a 0.1% aqueous formic acid solution, and the second solvent is a hydrophobic solvent, for example, a solution containing 0.1% formic acid and 99.9% acetonitrile.

The sample intake valve 200 is a value for receiving a sample to be analyzed from the sample injector 130 and injecting the same into the column selection valve 300. The sample intake valve 200 includes six ports, i.e., a sample inlet port 201 to which a sample is fed from the sample injector 130, a first sample loop connection port 202 and a second sample loop connection port 203 provided at both ends of the sample loop 210, a sample outlet port 204 for discharging the remaining sample, a solvent inlet port 205 which is connected to the first pump 110 and to which a first solvent or a mixed solution containing the first solvent and a second solvent is fed, and a solvent outlet port 206 connected to the column selection valve 300.

When the sample inlet port 201, the first sample loop connection port 202, the second sample loop connection port 203 and the sample outlet port 204 are in fluid-communication with one another in the sample intake valve 200, the sample fed from the sample injector 130 can be fed through the sample inlet port 201 to the sample loop 210.

When the concentration of the sample fed through the sample loop 210 is excessively low, a user repeatedly injects the sample several times through the sample injector 130, thereby acquiring a sufficient sample concentration.

In addition, when feeding the sample to the sample loop 210 and storing the sample, the sample intake valve 200 can feed the sample to the sample loop 210 together with the first solvent to the column selection valve 300 using the solvent inlet port 205 and the solvent outlet port 206.

The column selection valve 300 is a valve connected to the second pump 120 and the sample intake valve 200, which includes four ports including a first inlet port 301 connected to the solvent outlet port 206 of the sample intake valve 200, a first outlet port 302 connected to one side of the dual column valve 400, a second inlet port 303 connected to the second pump 120 and a second outlet port 304 connected to the other side of the dual column valve 400.

The column selection valve 300 is connected to the second pump 120 and the sample intake valve 200 and selectively receives a sample together with the first solvent or a mixed solution containing the first solvent and the second solvent. The selectively fed sample, or the mixed solution containing the first solvent and the second solvent may be injected into the dual column valve 400, may then be separately eluted or be used for column equilibration.

The dual column valve 400 is a valve which includes ten ports provided along an edge thereof and selects fluid communication of conducting separate analysis on any one of the first column and the second column, while conducting cleaning and equilibration on the other column.

Specifically, the dual column valve 400 includes a first column port 401 connected to the first column, a solid phase extraction column selection port 402 and a solid phase extraction column channel port 404 constituting opposite ends of the first solid phase extraction column (SPE1), a solid phase extraction column inlet port 403 connected to the first outlet port 302 of the column selection valve 300 and selectively connected to the solid phase extraction column selection port 402 or a solid phase extraction column channel port 404, a first outlet port 405, a second outlet port 406, a second solid phase extraction column selection port 409 and a second solid phase extraction column channel port 407 constituting opposite ends of the second solid phase extraction column (SPE2), a second solid phase extraction column inlet port 408 connected to the second outlet port 304 of the column selection valve 300 and selectively connected to the second solid phase extraction column selection port 409 and the second solid phase extraction column channel port 407, and a second column port 410 connected to the second column.

For example, the dual column valve 400 can repeatedly conduct cleaning and equilibration by fluid communication with the second column or the second solid phase extraction column (SPE2) while conducting separate analysis of the sample by fluid communication with the first column or the first solid phase extraction column (SPE1), or can repeatedly conduct cleaning and equilibration by fluid communication with the first column or the first solid phase extraction column (SPE1), while conducting separate analysis by fluid communication with the second column or the second solid phase extraction column (SPE2).

Accordingly, the dual online liquid chromatography device according to an embodiment of the present invention can choose fluid communication of the first column or the first solid phase extraction column (SPE1) and fluid communication of the second column or the second solid phase extraction column (SPE2), using the column selection valve 300 and the dual column valve 400 and simultaneously conducts injection, desalting and concentration of the sample on any side of fluid communication to perform separate analysis, and injecting a mixed solution containing the first solvent and the second solvent into the other side of fluid communication to perform cleaning, and injecting a first solvent to perform equilibration.

Accordingly, the dual online liquid chromatography device according to an embodiment of the present invention reduces dead time taken for column equilibration to improve analysis efficiency.

[MODE FOR INVENTION]

Hereinafter, a control method including simultaneously conducting sample analysis and equilibration using a dual online liquid chromatography device according to an embodiment of the present invention will be described with reference to FIGS. 2A to 2E.

In the control method of the dual online liquid chromatography device according to an embodiment of the present invention, an operation of an initial mode is first conducted, as shown in FIG. 2A.

Specifically, the initial mode shown in FIG. 2A includes simultaneously conducting equilibration on a first column and a first solid phase extraction column (SPE1), equilibration on a second column and a second solid phase extraction column (SPE2) and storing a sample in a sample loop 210.

That is, the first solvent is injected from the first pump 110 by fluid communication of the first column and the first solid phase extraction column (SPE1) to conduct equilibration of the first column and the first solid phase extraction column (SPE1) and the first solvent is injected from the second pump 120 using fluid communication of the second column and the second solid phase extraction column (SPE2) to conduct equilibration of the second column and the second solid phase extraction column (SPE2).

In this case, optionally, equilibration may be conducted after cleaning the first column and the first solid phase extraction column (SPE1) by injecting a mixed solution containing the first solvent and the second solvent from the first pump 110 using fluid communication with the first column and the first solid phase extraction column (SPE1) and after cleaning the second column and the second solid phase extraction column (SPE2) by injecting a mixed solution containing the first solvent and the second solvent from the second pump 120 using fluid communication with the second column and the second solid phase extraction column (SPE2).

At the same time, the sample of the sample injector 130 is stored in the sample loop 210 through the sample inlet port 201. In this case, a sufficient amount of sample can be obtained by repeating injection of the sample several times through the sample injector 130.

After the initial mode, as shown in FIG. 2B, a first mode of the dual online liquid chromatography device according to an embodiment of the present invention is conducted.

The first mode includes injecting, desalting and concentrating the sample of the sample loop 210 together with the first solvent into the first solid phase extraction column (SPE1), while conducting equilibration on the second solid phase extraction column (SPE2).

Specifically, equilibration on the second solid phase extraction column (SPE2) is continuously conducted by forming fluid communication connected with the second solid phase extraction column inlet port 408, the second solid phase extraction column selection port 409, the second solid phase extraction column channel port 407 and the second outlet port 406 and injecting the first solvent from the second pump 120.

At the same time, the sample loop 210 injects the sample of the sample loop 210, together with the first solvent injected from the first pump 110, by fluid communication with the first solvent inlet port 205 and the first solvent outlet port 206, into the column selection valve 300.

The sample injected into the column selection valve 300 together with the first solvent is injected into the first solid phase extraction column (SPE1) via fluid communication connected between the solid phase extraction column inlet port 403, the solid phase extraction column selection port 402, the first solid phase extraction column (SPE1), the solid phase extraction column channel port 404 and the first outlet port 405 in the dual column valve 400. At this time, about 2 µl of the first solvent is for example further injected, so that salts are dissolved in a water-soluble solvent (the first solvent) and are then discharged through the first outlet port 405. Accordingly, the sample is desalted and concentrated in the first solid phase extraction column (SPE1).

After conducting the first mode of injecting the sample together with the first solvent into the first solid phase extraction column (SPE1), as shown in FIG. 2C, a second mode of the dual online liquid chromatography device according to an embodiment of the present invention is conducted.

The second mode may include simultaneously conducting separate elution of the sample injected into the first solid phase extraction column (SPE1) and cleaning and equilibrating the second column and the second solid phase extraction column (SPE2) and may then optionally include storing another sample in the sample loop 210.

Specifically, separate elution of the sample in the second mode is carried out while flowing a mixed solution containing the first solvent and the second solvent, by the second pump 120, to the first column via the second inlet port 303, the first outlet port 302, the solid phase extraction column inlet port 403, the solid phase extraction column channel port 404, the first solid phase extraction column (SPE1), the solid phase extraction column selection port 402 and the first column port 401, by switching the sample intake valve 200, the column selection valve 300 and the dual column valve 400.

At this time, separate elution of the sample in the first solid phase extraction column (SPE1) is carried out while changing ratios of the first solvent and the second solvent in the mixed solution supplied from the second pump 120 over time, as shown in "I" of FIG. 1. That is, as the ratio of the second solvent in the mixed solution increases, dissociation degree of the sample injected into the first solid phase extraction column (SPE1) is increased, the sample is injected into the first column and analysis is then conducted by separation of the sample.

Regarding the first solvent and the second solvent, a variety of combinations of solvents may be selected to accomplish the aforementioned object. The first solvent may be a 0.1% aqueous formic acid solution and the second solvent may be a 90% aqueous acetonitrile solution, but the present invention is not limited thereto. That is, the characteristics of the solvent are based on the property that, as the content of acetonitrile in the total solvent increases, the degree of dissociation of sample present in the first solid phase extraction column (SPE1) increases.

In addition, the cleaning and equilibrating the second column and the second solid phase extraction column (SPE2) in the second mode includes (i) cleaning including flowing a mixed solution containing the first solvent and the second solvent by the first pump 110 into the solvent inlet port 205, the solvent outlet port 206, the first inlet port 301, the second outlet port 304, the second solid phase extraction column inlet port 408, the second solid phase extraction column channel port 407, the second solid phase extraction column (SPE2), the second solid phase extraction column selection port 409, the second column port 410 and the second column wherein the content of the second solvent is increased for a short time; and (ii) equilibration including continuously flowing the first solvent by the first pump 110.

Optionally, the storing another sample in the second mode may include injecting another sample of the sample injector 130 via fluid communication formed by the sample inlet port 201, the first sample loop connection port 202, the second sample loop connection port 203 and the sample outlet port 204 and then storing the same in the sample loop 210, after cleaning and equilibrating the second column and the second solid phase extraction column (SPE2).

After the second mode, as shown in FIG. 2D, a third mode of the dual online liquid chromatography device according to an embodiment of the present invention is conducted.

The third mode includes switching the sample intake valve 200 and the dual column valve 400 to simultaneously conduct equilibration of the first solid phase extraction column (SPE1) and injection of another sample of the sample loop 210 together with the first solvent into the second solid phase extraction column (SPE2), and desalting and concentration.

Specifically, equilibration of the first solid phase extraction column (SPE1) in the third mode is carried out by feeding the first solvent by the second pump 120 using fluid communication connecting the second inlet port 303, the first outlet port 302, the solid phase extraction column inlet port 403, the solid phase extraction column selection port 402, the first solid phase extraction column (SPE1), the solid phase extraction column channel port 404 and the first outlet port 405.

In addition, injection of another sample of the sample loop 210 together with the first solvent into the second solid phase extraction column (SPE2), and desalting and concentration is carried out by forming fluid communication between the sample loop 210 storing another sample, and the first solvent inlet port 205 and the first solvent outlet port 206, to inject the sample together with the first solvent fed from the first pump 110 into the column selection valve 300.

The another sample injected into the column selection valve 300 together with the first solvent is injected into the second solid phase extraction column (SPE2) via fluid communication connected between the second solid phase extraction column inlet port 408, the second solid phase extraction column selection port 409, the second solid phase extraction column (SPE2), the second solid phase extraction column channel port 407 and the second outlet port 406 in the dual column valve 400.

Then, 2 µl of the first solvent is further injected from the first pump 110 via the fluid communication, so that salts are dissolved in a water-soluble solvent (the first solvent) and are then discharged through the second outlet port 406.

Accordingly, the sample is concentrated in the second solid phase extraction column (SPE2).

After completion of the third mode of injecting another sample of the sample loop 210 into the second solid phase extraction column (SPE2), as shown in FIG. 2E, a fourth mode of the dual online liquid chromatography device according to an embodiment of the present invention is conducted.

By switching the sample intake valve 200, the column selection valve 300 and the dual column valve 400, the fourth mode includes simultaneously conducting cleaning and equilibrating the first column and the first solid phase extraction column (SPE1) and separately eluting another sample injected into the second solid phase extraction column (SPE2), and may optionally include storing another sample in the sample loop 210.

Specifically, cleaning and equilibration of the first column and the first solid phase extraction column (SPE1) in the fourth mode includes (i) conducting cleaning while flowing the first solvent by the first pump 110 to the first column via the first solvent inlet port 205, the first solvent outlet port 206, the first inlet port 301, the first outlet port 302, the solid phase extraction column inlet port 403, the solid phase extraction column channel port 404, the first solid phase extraction column (SPE1), the solid phase extraction column selection port 402 and the first column port 401, wherein the content of the second solvent is increased for a short time and (ii) equilibration including continuously flowing the first solvent by the first pump 110.

In addition, separate elution of another sample injected into the second solid phase extraction column (SPE2) is carried out while flowing a mixed solution containing the first solvent and the second solvent by the second pump 120 to the second inlet port 303, the second outlet port 304, the second solid phase extraction column inlet port 408, the second solid phase extraction column channel port 407, the second solid phase extraction column (SPE2), the second solid phase extraction column selection port 409, the second column port 410 and the second column.

At this time, in separate elution of another sample, the dissociation degree of the another sample injected into the second solid phase extraction column (SPE2) can be increased by increasing a ratio of the second solvent in the mixed solution supplied from the second pump 120 over time, as shown in "II" of FIG. 1.

In such a fourth mode, optionally, storing another sample in the sample loop 210 by the sample injector 130 may be conducted. Another sample of the sample injector 130 may be injected by fluid communication including the sample inlet port 201, the first sample loop connection port 202, the second sample loop connection port 203 and the sample outlet port 204 and may then be stored in the sample loop 210.

The another sample injected and stored in the sample loop 210 may be subjected to the first mode shown in FIG. 2B and the second mode shown in FIG. 2C, so that separate elution and equilibration may be repeatedly conducted on the another sample, as shown in "III" of FIG. 1.

Accordingly, a method of controlling a dual online liquid chromatography device according to an embodiment of the present invention can improve analysis efficiency regardless of dead time by repeating initial to fourth modes depending on the frequency of separate analysis of samples or the number of samples injected by the sample injector 130.

The invention has been described in detail with reference to preferred embodiments thereof. However, it will be appreciated that changes may be made in these embodiments without departing from the principles and spirit of the invention, the scope of which is defined in the appended claims and their equivalents.

INDUSTRIAL APPLICABILITY

The present invention provides a dual online liquid chromatography device which conducts analysis test on a column at one side while conducting cleaning and equilibration on a column at the other side.

The invention claimed is:
1. A dual online liquid chromatography device comprising:
   a first pump for injecting a first solvent or a mixed solution containing the first solvent and a second solvent;
   a second pump for injecting the first solvent or the mixed solution containing the first solvent and the second solvent;
   a sample intake valve connected to the first pump and a sample injector for injecting a sample;
   a column selection valve connected to the second pump and the sample intake valve; and
   a dual column valve having one side connected to the column selection valve and the other side connected to a first column and a second column, and comprising a plurality of ports, wherein the dual column valve further comprises:
   a first column port connected to the first column;
   a solid phase extraction column selection port and a solid phase extraction column channel port constituting opposite ends of a first solid phase extraction column (SPE1);
   a solid phase extraction column inlet port connected to one side of the column selection valve and selectively connected to the solid phase extraction column selection port or the solid phase extraction column channel port;
   a first outlet port adjacent to the solid phase extraction column channel port;
   a second outlet port adjacent to the first outlet port;
   a second solid phase extraction column selection port and a second solid phase extraction column channel port constituting opposite ends of a second solid phase extraction column (SPE2);
   a second solid phase extraction column inlet port connected to the other side of the column selection valve and selectively connected to the second solid phase extraction column selection port and the second solid phase extraction column channel port; and
   a second column port connected to the second column.

2. The dual online liquid chromatography device according to claim 1, wherein the sample intake valve comprises:
   a sample inlet port to which the sample is fed from the sample injector;
   a first sample loop connection port and a second sample loop connection port provided at opposite ends of a sample loop;
   a sample outlet port for discharging the remaining sample;
   a solvent inlet port connected to the first pump and to which the first solvent or the mixed solution containing the first solvent and the second solvent is fed; and
   a solvent outlet port connected to the column selection valve.

3. The dual online liquid chromatography device according to claim 1, wherein the column selection valve comprises:

a first inlet port connected to the sample intake valve;
a first outlet port connected to one side of the dual column valve;
a second inlet port connected to the second pump; and
a second outlet port connected to the other side of the dual column valve.

4. The dual online liquid chromatography device according to claim 1, wherein the dual column valve forms a first fluid communication with the first column or the first solid phase extraction column (SPE1), and a second fluid communication with the second column or the second solid phase extraction column (SPE1), and the dual column valve selectively has a mode of simultaneously conducting separate analysis of the sample using the first fluid communication, and cleaning and equilibration of the second fluid communication, and a mode of simultaneously conducting separate analysis of the sample using the second fluid communication, and cleaning and equilibration of the first fluid communication.

5. A method of controlling a dual online liquid chromatography device comprising:
(A) conducting an initial mode comprising equilibration of a first column or a first solid phase extraction column (SPE1), equilibration of a second column and a second solid phase extraction column (SPE2) and storing a sample in a sample loop;
(B) conducting a first mode comprising injecting the sample of the sample loop into the first solid phase extraction column (SPE1) together with a first solvent;
(C) conducting a second mode comprising separate elution of the sample injected into the first solid phase extraction column (SPE1), cleaning and equilibration of the second column and the second solid phase extraction column (SPE2) and injecting and storing another sample into the sample loop;
(D) conducting a third mode comprising equilibration of the first solid phase extraction column (SPE1), and injecting the another sample of the sample loop together with the first solvent into the second solid phase extraction column (SPE2); and
(E) conducting a fourth mode comprising cleaning and equilibration of the first column and the first solid phase extraction column (SPE1) and separate elution of another sample injected into the second solid phase extraction column (SPE2).

6. The method according to claim 5, wherein the step (E) further comprises storing another sample in the sample loop.

7. The method according to claim 5, wherein the steps (A) to (E) are repeatedly conducted depending on the frequency of separate analysis of the sample or the number of the samples.

8. The method according to claim 5, wherein the step (A) comprises:
injecting the first solvent from a first pump using fluid communication with the first column and the first solid phase extraction column (SPE1) to conduct equilibration of the first column and the first solid phase extraction column (SPE1) by, and injecting the first solvent from a second pump using fluid communication with the second column and the second solid phase extraction column (SPE2) to conduct equilibration of the second column and the second solid phase extraction column (SPE2).

9. The method according to claim 5, wherein the step (A) further comprises:

(A-1) injecting the mixed solution containing the first solvent and a second solvent from a first pump using fluid communication with the first column and the first solid phase extraction column (SPE1) to conduct cleaning of the first column and the first solid phase extraction column (SPE1), and injecting the mixed solution containing the first solvent and the second solvent from a second pump using fluid communication with the second column and the second solid phase extraction column (SPE2) to conduct cleaning of the second column and the second solid phase extraction column (SPE2); and
(A-2) injecting the first solvent from the first pump using fluid communication with the first column and the first solid phase extraction column (SPE1) to conduct equilibration of the first column and the first solid phase extraction column (SPE1), and injecting the first solvent from the second pump using fluid communication with the second column and the second solid phase extraction column (SPE2) to conduct equilibration of the second column and the second solid phase extraction column (SPE2).

10. The method according to claim 5, wherein the step (B) further comprises:
further injecting the first solvent into the first solid phase extraction column (SPE1) so that salts are dissolved in the first solvent and discharged from the SPE1 through a first outlet port to concentrate and desalt the sample in the first solid phase extraction column (SPE1).

11. The method according to claim 5, wherein, in the step (C), separate elution of the sample injected into the first solid phase extraction column (SPE1) is carried out while flowing, by a second pump, a mixed solution containing the first solvent and a second solvent via the first solid phase extraction column (SPE1) to the first column,
wherein a ratio of the first solvent and the second solvent is changed over time.

12. The method according to claim 5, wherein, in the step (C), cleaning and equilibration of the second column and the second solid phase extraction column (SPE2) comprises:
cleaning including flowing, by a first pump, a mixed solution containing the first solvent and a second solvent via the second solid phase extraction column (SPE2) to the second column, while increasing a content of the second solvent; and
equilibration including continuously flowing the first solvent, by the first pump, via the second solid phase extraction column (SPE2) to the second column.

13. The method according to claim 5, wherein, in the step (D), the injecting another sample in the sample loop together with the first solvent into the second solid phase extraction column (SPE2) further comprises further injecting the first solvent into the second solid phase extraction column (SPE2) so that salts are dissolved in the first solvent and discharged through a second outlet port to concentrate and desalt the sample in the second solid phase extraction column (SPE2).

14. The method according to claim 5, wherein, in the step (E), the separate elution of another sample injected into the second solid phase extraction column (SPE2) is carried out while flowing a mixed solution containing the first solvent and a second solvent by a second pump via the second solid phase extraction column (SPE2) to the second column,
wherein a ratio of the first solvent and the second solvent is changed over time.

15. The method according to claim 5, wherein, in the step (E), the cleaning and equilibration of the first column and the first solid phase extraction column (SPE1) comprises:
- cleaning including flowing, by a first pump, a mixed solution containing the first solvent and a second solvent via the first solid phase extraction column (SPE1) to the first column, while increasing a content of the second solvent; and
- equilibration including continuously flowing the first solvent, by the first pump, via the first solid phase extraction column (SPE1) to the first column.

* * * * *